United States Patent [19]

Shuber

[11] Patent Number: 5,633,134

[45] Date of Patent: May 27, 1997

[54] METHOD FOR SIMULTANEOUSLY DETECTING MULTIPLE MUTATIONS IN A DNA SAMPLE

[75] Inventor: Tony Shuber, Milford, Mass.

[73] Assignee: IG Laboratories, Inc., Framingham, Mass.

[21] Appl. No.: 308,638

[22] Filed: Sep. 19, 1994

Related U.S. Application Data

[63] Continuation of Ser. No. 957,205, Oct. 6, 1992, abandoned.

[51] Int. Cl.$^6$ .................................................. C12Q 1/68
[52] U.S. Cl. .................................................. 435/6; 536/24.3
[58] Field of Search ............................... 435/6; 536/24.3

[56] References Cited

U.S. PATENT DOCUMENTS 4,683,195  7/1987  Mullis et al. ............................... 435/6

FOREIGN PATENT DOCUMENTS 0288075   7/1987   European Pat. Off. .
89310424.0 10/1989  European Pat. Off. .
90/01564   2/1990   WIPO .

OTHER PUBLICATIONS

Lichter et al., Science, 247:64–69, Jan. 5, 1990.

Ferrie, R.M. et al. "Development Multiplexing, And Application of Arms Test For Common Mutations In the CFTR Gene" American Journal of Human Genetics, 51:251–262, Aug., 1992.

Shuber, A. et al. (1991) "A Rapid Method For Simultaneous Analysis Of Multiple Point Mutations Within The CF Gene" The American Journal of Human Genetics, 49(4).

Nevinny–Stickel, C. et al. (1991) "Nonradioactive HLA Class II Typing Using Polymerase Chain Reaction And Diogoxigenin–11–2'3'–Dideoxyuridinetriphosphate–Labeled Oligonucleotide Probes" Human Immunology, 31:7–13.

Gogos J. A. et al. (1990) "Detection Of Single Base Mismatches Of Thymine And Cytosine Residues By Potassium Permanganate And Hydroxylamine In The Presence Of Tetralkylammonium Salts" Nucleic Acids Research, 18(23):6807–6814.

Hung, T. et al. (1990) "A Specificity Enhancer For Polymerase Chain Reaction" Nucleic Acids Research, 18(16):4953.

Devlin, P. E. et al. (1988) "Laboratory Methods—Southern Analysis of Genomic DNA With Unique And Degenerate Oligonucleotide Probes: A Method For Reducing Probe Degeneracy" DNA, 7(7):449–507.

Jacobs, K. A. et al. (1988) "The Thermal Stability Of Oligonucleotide Duplexes Is Sequence Independent In Tetraalkylammonium Salt Solutions: Application To Identifying Recombinant DNA Clones" Nucleic Acids Research, 16(10):4637–4650.

Marky, L. A. et al. (1988) "Differential Effect Of Tetramethylammonium Chloride And Sodium Chloride On Duplex Melting Temperatures Of Deoxyoligonucleotides: Resolution Of A Salt Effect Into Specific And Non-specific Components" Can. J. Chem, 66:836–838.

DiLella, A. G. and Woo, S.L.C. (1987) "Hybridization of Genomic DNA To Oligonucleotide Probes In The Presence Of Tetramethylammonium Chloride" Methods In Enzymology, 152:447–451.

Wood, W. I. et al. (1985) "Base Composition–Independent Hybridization In Tetramethylammonium Chloride: A Method For Oligonucleotide Screening Of Highly Complex Gene Libraries" Proc. Natl. Acad. Sci USA, 82:1585–1588.

Marky, L. A. et al. (1981) "Effect of Tetramethylammonium Ion On The Helix–To–Coil Transition Of Poly(deoxyadenylylthymidine): A Nuclear Magnetic Resonance And Calorimetric Investigation" Biochemistry, 20:1427–1431.

Primary Examiner—Scott W. Houtteman
Attorney, Agent, or Firm—Darby & Darby

[57] ABSTRACT

The invention provides a rapid, cost-effective process for simultaneously testing large numbers of individuals for the presence or absence of multiple mutaitons in one gene or multiple genes using allele specific oligonucleotide (ASO) probes in the presence of a quaternary ammonium salt which eliminates disparities in the melting temperatures of the ASO used.

20 Claims, No Drawings

METHOD FOR SIMULTANEOUSLY DETECTING MULTIPLE MUTATIONS IN A DNA SAMPLE

This is a continuation of application Ser. No. 07/957,205, filed Oct. 6, 1992 now abandoned.

BACKGROUND

The ability to detect differences in DNA sequence (i.e. mutations) is of great importance in the field of medical genetics. For example, the detection of mutations directly in genomic DNA is essential for identifying polymorphisms for genetic studies, to determine the molecular basis of inherited diseases and to provide carrier and prenatal diagnosis for genetic counselling. Traditionally, detection of DNA variation has been performed by analysis of RFLPs using the Southern blotting technique (Southern. EM *J Mol Biol* 98:503–517 (1975)): Kan Y and A Dozy *Nature* 313:369–374 (1978); Wyman, A. and R. White *Proc Natl. Acad. Sci. USA* 77:6754–6758 (1980)). However, as this approach is relatively slow and technically demanding, new methods based on the polymerase chain reaction have been developed. These include (RFLP) analysis (Chehab et. al. *Nature* 329:293–294 (1987), the creation of artificial RFLPs by the use of primer-specified restriction-map modification (Hallassos A. et. al. *Nucleic Acids Res.* 17:3606 (1989)), hybridization to allele-specific oligonucleotides (ASOs) (Saiki et. al. *Nature* 324:163–166 (1986)) or detection of small deletions by determination of the size of the PCR product (Rommens et. al. *Am J. Hum Genet* 46:395–396 (1990)). Of these methods, only the ASO approach can be used to detect any point mutation or small deletion, as the other methods are all dependent on the nature of the mutation and the surrounding DNA sequence.

It is now becoming clear that, for many genetic diseases, there is more than one mutation responsible for the condition. For example, to date more than 225 cystic fibrosis (CF) disease causing mutations have been reported (CF Genetic Analysis Consortium, unpublished data), while not accounting for all cases of CF. Furthermore, the mutations can be closely spaced often within a few base pairs of each other. Examples of multimutational diseases include CF (Cutting G. et. al. *Nature* 346:366–369 (1990)); β-thalassaemia (Old JM et. al. *Lancet* 336:834–837 (1990)) Tay-Sachs disease (Myerowitz R. *Proc Natl Acad Sci* USA 85:3955–3959 (1988)) and Sickle cell anemia (Saiki, R. K. et. al. *Science* 230, 1350–1354 (1985)). The presence of multiple potential mutations makes the detection of these diseases complex.

A method which enables the simultaneous analysis of a sample for the presence of multiple mutations would be useful.

SUMMARY OF THE INVENTION

In general, the invention relates to a process for analyzing a DNA sample for the presence of multiple mutations simultaneously using allale specific oligonucleotide probes (ASOs).

According to the process, a DNA sample is hybridized with multiple mutation specific ASO probes of approximately the same length in the presence of an agent that eliminates disparities in ASO melting temperatures under stringent hybridization conditions. After an appropriate period of time, the sample can be washed to remove unhybridized ASO probes and the presence or absence of hybridization detected. The detection of hybridization being indicative of the presence of at least one mutation in the DNA sample.

In a preferred embodiment, the agent that eliminates disparities in ASO melting temperatures is a quaternary ammonium salt such as tetramethyl ammonium chloride (TMAC), which is included in the hybridization buffer. In a further preferred embodiment, the hybridization buffer additionally includes unlabelled allale specific oligonucleotides or fragments thereof which are complimentary to the normal, wild-type allale specific sequences.

The method described herein provides a rapid, cost-effective means to screen large numbers of samples simultaneously for multiple mutations including point mutations and small deletions at a particular genetic disease locus at one time, as well as multiple mutations in different genes located on the same or on different chromosomes.

DETAILED DESCRIPTION OF THE INVENTION

The invention is predicated on the surprising finding that in the presence of an agent that eliminates disparities in melting temperatures, multiple allele specific oligonucleotide (ASO) probes recognizing multiple regions on the same gene or multiple genes on the same or different chromosomes and having varying GC base-pair contents can be simultaneously hybridized under stringent conditions to a sample DNA. This result is surprising, since previously, for each ASO probe used in an assay, a separate hybridization reaction and wash procedure was required.

Based on this finding, the invention features, in general, a process for simultaneously detecting the presence or absence of multiple mutations (i.e. more than one mutation) in a DNA sample by hybridizing the sample with multiple allele specific oligonucleotide probes of approximately the same length under stringent conditions in the presence of an appropriate concentration of an agent that eliminates disparities in melting temperature and detecting hybridization as an indication of the presence of at least one mutation in the sample.

As used herein, the term "mutation" is meant to refer to a change in the base sequence of DNA from the normal, wild-type sequence. The most common mutations are substitutions, additions (i.e. insertions); rearrangements and deletions of one or more base. The term "point mutation" is generally used to denote a change in a single base pair.

For use in the invention, a DNA sample may be obtained from any cell source using methods which are well known in the art. For example, DNA can be obtained from: (i) blood leukocytes obtained from whole blood (e.g. via centrifugation); (ii) buccal cells obtained using a swab or cytobrush as described in Example 1 herein or using a mouthwash technique (Lench, N. et. al. *The Lancet* 1:1356–8 (Jun. 18, 1988,)); (iii) cervicovaginal cells obtained using a brush, swab or lavage (Burk, R. D. and C. Spitzer *Am J Obstet Gynecol.* 162:652–4 (1990); (iv) epithelial cells obtained from urine (Gasparini, P. et. al. *N. Engl. J. Med* 320:809 (1989) or hair roots (Higuchi, R. et. al. *Nature* 332:543–6 (1988); (v) fetal cells obtained from amniotic fluid, cord blood, chorionic villus tissue, cervical secretions or maternal blood (Bianchi, D. W. et. al *Proc. Natl. Acad. Sci. USA* 87:3279–83 (1990); and (vi) embryonic cells obtained from biopsied embryos.

Once obtained, a DNA sample can be prepared for hybridization using techniques which are well-known to one of skill in the art. For example, in order to increase the amount of DNA available for hybridization and thereby the signal obtained, amplification procedures, such as the polymerase chain reaction (PCR) can be employed (Saiki, R. K. et. al. *Science* 239:487–491 (1988)).

ASOs to be used in the subject invention can be designed to identify allele specific mutations of a gene. Preferably ASOs are synthesized in appropriate amounts, for example using a DNA synthesizer. ASOs can then be labelled with a detectable marker to generate ASO probes according to procedures which are well known in the art. Traditionally, ASOs have been radioactively end-labelled (e.g. using $^{32}$P or $^{35}$S). However, ASOs can also be labelled by non-isotopic methods (e.g. via direct or indirect attachment of fluorochromes or enzymes, or by various chemical modifications of the nucleic acid fragments that render them detectable immunochemically or by other affinity reactions).

ASOs which are to be used in a pool to detect multiple mutations in the same hybridization reaction according to the method of the subject invention, should all be approximately of the same length (i.e. approximately the same number of base pairs). The appropriate concentration of a particular ASO to be used in a pool can be determined empirically without requiring undue experimentation. For example, the optimal concentrations of each ASO used in a pool to probe the cystic fibrosis transmembrane regulator gene, as set forth in the following Example 1, was initially tested at a concentration of 0.03 pmol. If the signal produced was too light, the concentration was doubled until the appropriate signal intensity was obtained. It is important to point out that if the concentration of ASO used is too high, background noise will result.

Hybridization between sample DNA and appropriate ASO probes (i.e. labelled allele specific oligonucleotides of approximately the same length) can be carried out in a hybridization buffer containing an agent that eliminates disparities in the melting temperature of the ASOs used. One preferred agent is a quaternary ammonium salt (e.g. tetramethyl ammonium chloride, tetraethyl ammonium chloride, tetramethyl ammonium fluoride or tetraethyl ammonium fluoride).

Tetramethyl ammonium chiodde (TMAC) has been found to be an especially preferred quaternary ammonium salt for use in the subject invention. When added to hybridization buffer in a concentration in the range of about 2–5 M and optimally about 3 M, TMAC has been found to eliminate disparities in the melting temperatures of multiple ASOs, allowing the stringency of hybridization to be controlled as a function of probe length alone regardless of GC content (Wood, W. I. Proc. Natl. Acad. Sci. USA 82:1585–1588 (1985)). In addition to being present in the hybridization buffer, the quaternary ammonium salt may also be present in the wash solution, that is used to remove unbound nucleotides following hybridization. Further, it has been reported that TMAC in the PCR mixture can dramatically reduce and even eliminate non-specific priming events, thereby enhancing the specificity of the reaction (Hung, T. et. al. Nucl. Acid Res. 18:4953 (1990)).

In order to increase the signal to noise ratio, hybridization and washes should be carried out under stringent conditions. In other words, the temperature at which the hybridization reaction is conducted should be as high as possible for the length of ASO being used. The appropriate stringency for a particular ASO pool can be determined empirically. As an example, for the 17 base pair ASOs used to probe the cystic fibrosis transmembrane regulator gene, hybridizations were carried out at 52° C.

It has been found that signal to noise ratios of hybridized mutation specific ASOs can be further increased by including cold (i.e. non-labelled), normal (i.e. wild-type) oligonucleotides or portions thereof to the hybridization reaction preferably in a concentration in the range of about 1–100 times the concentration of labelled ASO. Presumably, unlabelled normal oligonucleotides or nucleotide portions outcompete the mutation specific labelled ASOs, where normal sequence is present thereby reducing the degree of non-specific hybridization occurring between the mutation specific ASOs and the normal wild-type sequence.

Subsequent to a wash step, hybridization can be detected using a means which is appropriate for the particular label used. For example, if ASOs are labelled radioactively, hybridization can be detected using autoradiography.

The procedure described herein can be used to test large numbers of samples simultaneously for multiple mutations within a gene. In addition, it can be used to simultaneously analyze several different individuals who have different disease indications (e.g. cystic fibrosis, sickle cell anemia, β-thallasemia, Tay-Sachs, Gaucher's disease and cancers resulting from certain mutations in genes, such as the P-53 gene) in a single hybridization assay and yet achieve disease specific results.

The present invention will now be illustrated by the following examples, which are not Intended and should not be construed as being limited in any way.

EXAMPLE 1

Efficient Multi-Mutation Testing in the Cystic Fibrosis Transmembrane Regulator (CFTR) Gene Preparation of Sample DNA from CF Patient Blood Whole blood samples collected in high glucose ACD Vacutainers™ (yellow top) were centrifuged and the buffy coat collected. The white cells were lysed with two washes of a 10:1 (v/v) mixture of 14 mM NH$_4$Cl and 1 mM NaHCO$_3$, their nuclei were resuspended in nuclei-lysis buffer (10 mM Tris, pH 8.0, 0.4 M NaCl, 2 mM EDTA, 0.5% SDS, 500 ug/ml proteinase K) and incubated overnight at 37° C. Samples were then extracted with a one-fourth volume of saturated NaCl and the DNA was precipitated in ethanol. The DNA was then washed with 70% ethanol, dried, and dissolved in TE buffer (10 mM Tris-HCl, pH 7.5, 1 mM EDTA).

Preparation of Sample DNA from Buccal Cells

Buccal cells were collected on a sterile cytology brush (Scientific Products #S7766-1A) or female dacron swab (Medical Packaging Corp. #DTS-100), by twirling the brush or swab on the inner cheek for 30 seconds. DNA was prepared from the cheek cells, immediately or after a period of storage at room temperature or 4° C.: the brush or swab was immersed in 600 ul of 50 mM NaOH contained in a polypropylene microcentrifuge tube, and vortexed. The tube, still containing the brush or swab, was heated at 95° C. for 5 min., after which the brush/swab was carefully removed, leaving behind any residual liquid in the tube. The DNA solution was then neutralized with 60 ul of 1 M Tris, pH 8.0, and vortexed again (Mayall, E. and Williams, C. J. Med. Genet. 27:658 (1990)). After preparation, the buccal cell DNA was stored at 4° C., and 10 ul was used in a 50 ul PCR reaction.

Sample Amplification and Dot Blotting

Patient DNA samples were amplified in duplicate by PCR (Saiki, R. K. et. al., Science 239:487–491 (1988)) in a Perkin-Elmer Cetus 9600 Thermocycler. Five primer sets were used simultaneously to amplify regions of exons 4, 10, 11, 20, and 21 in a 50 ul reaction volume containing 200 ng of sample DNA and the following components; 10 mM Tris, pH 8.3, 50 mM KCl, 1.5 mM MgCl$_2$, 0.01% gelatin, 200 uM in each dNTP, 0.4 uM in each amplification primer, and 2.5 units of Taq polymerase enzyme (Multiplex conditions were slightly modified by using 2.5 mM $MgCl_2$, 5 units of Taq polymerase, and 10 ul of human genomic DNA prepared from cheek cells in a 50 ul reaction, or 1 ug of DNA prepared from blood). An initial denaturation of 20 sec. at 94° C. was done, followed by 28 cycles of amplification consisting of 10 sec. at 94° C., 10 sec. at 55° C., 10 sec. at 74° C., and a final soak at 74° C. for 5 min. Following amplification, 8 ul of the PCR product were electrophoresed on a 2% agarose gel to verify the presence of all five products and 8 ul of the mixed PCR products were added to 50 ul of denaturation solution (0.5 M NaOH, 2.0 M NaCl, 25 mM EDTA). The amplified products were spotted onto four nylon membranes (INC Biotrans), using a 96-well dot-blot apparatus (Bethesda Research Laboratories). The DNA was subsequently fixed to the membranes by baking the filters in vacuum at 80° C. for 15 min.

Hybridization and Washing $^{32}$P-labeled mutation specific ASO probes: were made from the ASO sequences shown In Table 1.

all of the hybridizations and washes to be performed at the same temperature (52° C.), despite a range in G-C content from 30% to 53% (Table 1).

CF/12 Test Design

Pools of ASOs were generated for more efficient mutation analysis. The compositions of the pools were determined by the total number of ASOs to be used in the assay, and by the estimated frequency of each mutation among Caucasian CF patients of northern European decent (Table 2). The frequency of each mutation determined how often it was necessary to follow up a pool-positive result with individual ASO hybridizations.

TABLE 2

Pool Design Considerations

1) Number of ASOs (N = 12)
2) Mutation Frequencies

| Mutation | # of CF Chromosomes | Frequency |
| --- | --- | --- |

TABLE 1

| Mutation | ASO Sequence | GC Content/ASO % |
| --- | --- | --- |
| G542X | ATTCCACCTTCTCAAAG (SEQ ID NO:1) | 40 |
| G551D | CTCGTTGATCTCCACTC (SEQ ID NO:2) | 53 |
| R553X | CTCATTGACCTCCACTC (SEQ ID NO:3) | 53 |
| W1282X | CTTTCCTCCACTGTTGC (SEQ ID NO:4) | 47 |
| N1303K | TCATAGGGATCCAAGTT (SEQ ID NO:5) | 41 |
| Δ1507 | ACACCAAAGATATTTTC (SEQ ID NO:6) | 30 |
| 1717-1 | GGAGATGTCTTATTACC (SEQ ID NO:7) | 41 |
| R560T | TATTCACGTTGCTAAAG (SEQ ID NO:8) | 53 |
| S549N | CTCGTTGACCTCCATTC (SEQ ID NO:9) | 53 |
| R117H | CGATAGAGTGTTCCTCC (SEQ ID NO:10) | 47 |
| 621 + 1 | GCAAGGAAGTATTACCT (SEQ ID NO:11) | 30 |

Hybridizations were carried out in plastic bags containing pooled $^{32}$p-labelled ASO probes shown in Table 1 and an excess of unlabeled normal sequences in a TMAC (Fisher Scientific) hybridization buffer (3.0 M TMAC, 0.6% SDS, 1.0 mM EDTA, 10 mM $Na_3PO_4$, pH 6.8, 5X Denhardt's solution, 40 ug/ml yeast RNA). ASO concentrations in the pools ranged from 0.03 to 0.15 pmol/ml of hybridization solution. The appropriate concentration for any particular ASO was determined empirically by testing the signal to noise ratio at an initial concentration of 0.03 and doubling the concentration until a proper signal to noise ratio was obtained. The bags were held overnight with agitation at 52° C. The membranes were then washed for 20 min. at room temperature with TMAC wash buffer (3.0 M TMAC, 0.6% SDS, 1.0ram EDTA, 10 mM $Na_3PO_4$, pH 6.8), followed by a second 20 min. TMAC wash at 52° C. The membranes were then dried and autoradiographs prepared by exposure to Kodak X-OMAT AR X-ray film.

Results

TMAC Properties and Hybridization Conditions

The specificity of hybridization in the presence of TMAC was established by probing amplified samples from individuals of known genotype with 11 of the 12 mutation-specific ASOs described above. Each ASO hybridized specifically only to samples carrying the complementary mutant sequence and not to samples which did not carry the complementary mutant sequence. Furthermore, the presence of TMAC in the hybridization and wash solutions allowed TABLE 2-continued Pool Design Considerations

| | | |
| --- | --- | --- |
| Δ508 | 548 | 72.0% |
| G551D | 15 | 2.0% |
| G542X | 13 | 1.7% |
| W1282X | 15 | 2.0% |
| N1303K | 12 | 1.5% |
| R553X | 9 | 1.1% |
| 621 + 1 | 9 | 1.1% |
| R117H | 3 | 0.4% |
| 1717 − 1 | 3 | 0.4% |
| R560T | 2 | 0.3% |
| Δ1507 | 1 | 0.1% |
| S549N | 1 | 0.1% |
| Unknown | 133 | 17.0% |
| Total | 764 | |

Conclusion (4 hybridizations)

| Filter # | 1 | 2 | 3 | 4 |
| --- | --- | --- | --- | --- |
| | Wild-type at 508 position | Δ508 | G551 D<br>G542X<br>W1282X<br>N1303K<br>R553X | 621 + 1<br>R117H<br>1717 − 1<br>R560T<br>Δ507<br>S549N |

*Minimal Number of Independent Hybridizations

Based on the foregoing considerations, analysis of the 12 mutations was broken into four individual hybridizations. As seen in Table 2, one of four identical filters was hybridized with a probe for the normal sequence at 508 position, with a second filter being hybridized only with a probe for the delta F508 mutation. A third was hybridized with a pool of ASOs for the five most frequent CFTR mutations after ΔF508:G551 D, G542X, W1282X, N1303K, and R553X. The fourth filter was probed with the remaining six mutations: 621+1, R117H, 1717-1, R560T, A1507, and S549N. The use of one filter for the normal 508 sequence and one for the ΔF508 mutation permitted immediate identification of all individuals affected with the most common mutation, as well as heterozygotes, these being the most widespread genotypes. Results from all four hybridizations were read in a binary manner. Each patient was represented by a pair of results, as samples were run in duplicate. Two critical quality-control Issues were addressed with this assay design. First, all samples were processed in duplicate, beginning with independent DNA extractions, followed by duplicate amplifications and analysis. This ensured against sample confusion at any of the sample-transfer steps. Second, each of the four independent filters contained a row of control samples of known genotype to ensure that each ASO within the respective pool had hybridized to its complimentary mutant sequence. These were the same samples used to determine the specificities of the ASOs.

Mutation Identification by Independent Hybridizations

Pool-positive samples were subsequently hybridized independently with the relevant ASOs to identify the specific mutation or mutations involved. Samples from patients with clinical indications of CF that were positive for only one of the pooled ASOs were then hybridized with the corresponding normal sequence to establish or exclude homozygosity for the mutation.

Validation Study

The use of pooled ASOs was validated by analyzing 382 DNA samples from CF-affected individuals, thereby obtaining data on 764 CFTR alleles. Secondary independent hybridizations of all pool-positive samples demonstrated that pool-positive results from these samples were due to the presence of one of the 12 mutations and not to non-specific hybridization. The detection frequencies observed in this study for the 12 mutations are given in Table 2.

Pool Complexity

For CFTR gene carder analysis in a clinical lab, there is a rationale for limiting the pools of ASOs to 5 or 6: it is necessary to be able subsequently to specify which ASO hybridized to a given positive sample. However, for other applications of the TMAC methodology, larger pools may be of great value. Therefore, the degree of pool complexity which could be attained pooling 11 of the 12 ASOs used in this study was tested. This pool was hybridized to a filter containing positive and negative control samples. The positive control samples were detected using the pool of probes. The negative control samples exhibited no significant non-specific hybridization. In other experiments, 14 ASOs have been hybridized simultaneously without non-specific hybridization.

EXAMPLE 2

Efficient Multi-Mutation Testing in the CFTR Gene and Gene for Sickle Cell Anemia The same protocol was followed as in Example 1, except that into the Δ508 hybridization (Table 2) was added an allele specific oligonucleotide probe "A" (wild-type) made from an ASO having the sequence: CTCCTCAGGAGT-CAGGT (SEQ ID NO:12) complementary to the normal, wild-type sequence within the β-globin gene and oligonucleotide probes "S" made from an ASO having the sequence: CTCCACAGGAGTCAGGT (SEQ ID NO:13) and "C" made from an ASO having the sequence: CTCCTTAG-GAGTCAGGT (SEQ ID NO:14) were added to hybridizations #3 and #4 respectively, (Table 2). This allowed individual samples suggestive of containing a mutation within the β-globin gene (Chromosome 11) to be analyzed simultaneously in the same hybridization as individuals suggestive of carrying a mutation in the CFTR gene (Chromosome 7).

Equivalents

Those skilled in the art will recognize or be able to ascertain using no more than routine experimentation; many equivalents to the specific embodiments of the invention described specifically herein. Such equivalents are intended to be encompassed in the scope of the following claims.

I claim:

1. A method of screening to simultaneously detect multiple target sequences of interest in genomic DNA, the method comprising:
  (a) immobilizing on a single solid support a sample of genomic DNA to be screened for said multiple target sequences of interest,
  (b) contacting said support with a pool of oligonucleotide probes of approximately the same length under stringent conditions in the presence of a concentration of about 2–5 M of a quaternary ammonium salt that allows the hybridization of said probes to DNA under said stringent conditions,
    wherein said pool comprises individual allele-specific oligonucleotide (ASO) probes, each ASO complementary to and specific for one of said multiple target sequences of interest suspected to be present in said DNA;
  (c) removing probes that do not hybridize to said DNA under said stringent conditions; and
  (d) detecting hybridization, wherein said hybridization indicates the presence of at least one of said multiple target sequences of interest in said DNA.

2. A method according to claim 1, wherein said multiple target sequences of interest are located within different regions of a gene present in said DNA.

3. A method according to claim 1, wherein said multiple target sequences of interest are located within multiple genes present in said DNA.

4. A method according to claim 1, wherein in step (a) a second genomic DNA sample is separately immobilized on said solid support.

5. A method according to claim 1, wherein in step (c) said unhybridized probes are removed in the presence of a concentration of about 2–5 M of a quaternary ammonium salt that prevents cross-hybridization of probes to non-complementary sequences.

6. A method according to claim 1 or 5, wherein the quaternary ammonium salt is tetramethyl ammonium chloride (TMAC).

7. A method according to claim 5, wherein said non-complementary sequences are selected from the group consisting of DNA sequences that differ from one or more of said target sequences by having a single nucleotide substitution, deletion, or addition, overlapping sequences and unrelated sequences.

8. A method according to claim 1, wherein said multiple target sequences of interest are polymorphic loci.

9. A method according to claim 8, wherein said polymorphic loci are associated with one or more multimutational disease.

10. A method according to claim 9, wherein said multimutational disease is selected from the group consisting of Cystic Fibrosis, β-thalassaemia, Tay-Sachs disease, Sickle cell anemia, Gaucher's disease and cancers.

11. A method of screening to simultaneously detect multiple target sequences of interest in genomic DNA, the method comprising:
  (a) immobilizing on a single solid support a sample of genomic DNA to be screened for said multiple target sequences of interest,
  (b) contacting said support with a pool of oligonucleotide probes of approximately the same length under stringent conditions in the presence of a concentration of about 2–5 M of a quaternary ammonium salt that allows the hybridization of said probes to DNA under said stringent conditions,
    wherein said pool comprises individual allele-specific oligonucleotide (ASO) probes, each ASO complementary to and specific for one of said multiple target sequences of interest suspected to be present in said DNA;
  (c) removing probes that do not hybridize to said DNA under said stringent conditions,
  (d) detecting hybridization, wherein said hybridization indicates the presence of at least one of said multiple target sequences of interest in said DNA,
  (e) contacting said DNA having at least one of said multiple target sequences of interest with an individual ASO probe under stringent conditions, wherein said contacting occurs in the presence of a concentration of a quaternary ammonium salt that allows the hybridization of said probe to DNA under said stringent conditions, and (f) detecting hybridization, wherein said hybridization indicates the presence of a target sequence complementary to said individual ASO probe in said DNA.

12. A method according to claim 11, wherein said multiple target sequences of interest are located within different regions of a gene present in said DNA.

13. A method according to claim 11, wherein said multiple target sequences of interest are located within multiple genes present in said DNA.

14. A method according to claim 11, wherein in step (a) a second genomic DNA sample is separately immobilized on said solid support.

15. A method according to claim 11, wherein in step (c) said unhybridized probes are removed in the presence of a concentration of about 2–5 M of a quaternary ammonium salt that prevents cross-hybridization of probes to non-complementary sequences.

16. A method according to claim 11 or 15, wherein the quaternary ammonium salt is tetramethyl ammonium chloride (TMAC).

17. A method according to claim 15, wherein said non-complementary sequences are selected from the group consisting of DNA sequences that differ from one or more of said target sequences by having a single nucleotide substitution, deletion, or addition, overlapping sequences, and unrelated sequences.

18. A method according to claim 11, wherein said multiple target sequences of interest are polymorphic loci.

19. A method according to claim 18, wherein said polymorphic loci are associated with one or more multimutational disease.

20. A method according to claim 19, wherein said multimutational disease is selected from the group consisting of Cystic Fibrosis, β-thalassaemia, Tay-Sachs disease, Sickle cell anemia, Gaucher's disease and cancers.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

ATTCCACCTT CTCAAAG                                                     17

( 2 ) INFORMATION FOR SEQ ID NO:2:

( i ) SEQUENCE CHARACTERISTICS:
        ( A ) LENGTH: 17 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:2:

CTCGTTGATC TCCACTC                                                      17

(2) INFORMATION FOR SEQ ID NO:3:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:3:

CTCATTGACC TCCACTC                                                      17

(2) INFORMATION FOR SEQ ID NO:4:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:4:

CTTTCCTCCA CTGTTGC                                                      17

(2) INFORMATION FOR SEQ ID NO:5:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:5:

TCATAGGGAT CCAAGTT                                                      17

(2) INFORMATION FOR SEQ ID NO:6:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:6:

ACACCAAAGA TATTTC                                                       17

(2) INFORMATION FOR SEQ ID NO:7:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA ( x i ) SEQUENCE DESCRIPTION: SEQ ID NO:7:

GGAGATGTCT TATTACC                                                                                                     17

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

TATTCACGTT GCTAAAG                                                                                                     17

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

CTCGTTGACC TCCATTC                                                                                                     17

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

CGATAGAGTG TTCCTCC                                                                                                     17

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GCAAGGAAGT ATTACCT                                                                                                     17

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

CTCCTCAGGA GTCAGGT                                                                                                     17

( 2 ) INFORMATION FOR SEQ ID NO:13:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:13:

CTCCACAGGA GTCAGGT                    17

( 2 ) INFORMATION FOR SEQ ID NO:14:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:14:

CTCCTTAGGA GTCAGGT                    17